US010163208B2

(12) United States Patent
Averkiou et al.

(10) Patent No.: US 10,163,208 B2
(45) Date of Patent: Dec. 25, 2018

(54) EVALUATION OF CAROTID PLAQUE USING CONTRAST ENHANCED ULTRASONIC IMAGING

(71) Applicant: KONINKLIJKE PHILIPS N.V., Eindhoven (NL)

(72) Inventors: Michalakis Averkiou, Lakatamia (CY); Damianos Christophides, Nicosa (CY); Edward Lam Shang Leen, Beaconsfield (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/112,290

(22) PCT Filed: Jan. 21, 2015

(86) PCT No.: PCT/IB2015/050452
§ 371 (c)(1),
(2) Date: Jul. 18, 2016

(87) PCT Pub. No.: WO2015/110961
PCT Pub. Date: Jul. 30, 2015

(65) Prior Publication Data
US 2016/0343134 A1   Nov. 24, 2016

Related U.S. Application Data

(60) Provisional application No. 61/930,655, filed on Jan. 23, 2014.

(51) Int. Cl.
*G06K 9/00* (2006.01)
*G06T 7/00* (2017.01)
(Continued)

(52) U.S. Cl.
CPC ............. *G06T 7/0016* (2013.01); *A61B 8/06* (2013.01); *A61B 8/4444* (2013.01);
(Continued)

(58) Field of Classification Search
CPC ........... A61B 8/06; A61B 8/461; A61B 8/481; A61B 8/4444; A61B 8/4494;
(Continued)

(56) References Cited

U.S. PATENT DOCUMENTS 5,570,430 A * 10/1996 Sheehan ............... G06T 7/0012
378/98.5
5,833,613 A 11/1998 Averkiou et al.
(Continued)

OTHER PUBLICATIONS

Akkus etal., "New Quantification Methods for Carotid Intra-Plaque Neovascularization Using Contrast-Enhanced Ultrasound", 2014 World Federation for Ultrasound in Medicine & Biology. Published by Elsevier, pp. 25-36.*

(Continued)

*Primary Examiner* — Mekonen Bekele (57) ABSTRACT

An ultrasound system and method are described for acquiring a sequence of ultrasound images of the carotid artery during the delivery of a contrast agent. Plaque in the images is identified and a time-intensity curve is calculated for pixels in the images. The intensity values before and after the arrival of contrast are compared to identify pixels or groups of pixels having perfusion. An anatomical image may be formed showing areas in an image of the plaque of the intensity and presence of perfusion, or the perfusion may be quantified by determining the percentage of pixels in the plaque image which exhibit perfusion. The extent and degree of perfusion is an indicator of the risk of plaque particulates in the blood stream which may lead to stroke-related symptoms.

15 Claims, 5 Drawing Sheets

(51) Int. Cl.
*A61B 8/06* (2006.01)
*A61B 8/00* (2006.01)
*A61B 8/08* (2006.01)
*G06K 9/62* (2006.01)
*G06T 7/20* (2017.01)
*H04N 5/232* (2006.01)

(52) U.S. Cl.
CPC ............ *A61B 8/4494* (2013.01); *A61B 8/461* (2013.01); *A61B 8/481* (2013.01); *A61B 8/5223* (2013.01); *G06K 9/6215* (2013.01); *G06T 7/20* (2013.01); *H04N 5/23267* (2013.01); *G06T 2207/10132* (2013.01); *G06T 2207/10136* (2013.01); *G06T 2207/20021* (2013.01); *G06T 2207/30101* (2013.01); *G06T 2207/30104* (2013.01)

(58) Field of Classification Search
CPC .. A61B 5/5223; G06K 9/6215; G06T 7/0016; G06T 7/20; G06T 2207/10132; G06T 2207/10136; G06T 2207/20021; G06T 2207/30101; G06T 2207/30104; H04N 5/23267
See application file for complete search history.

(56) References Cited

U.S. PATENT DOCUMENTS

| | | | |
|---|---|---|---|
| 6,013,032 A | 1/2000 | Savord | |
| 6,186,950 B1 | 2/2001 | Averkiou et al. | |
| 6,375,617 B1 | 4/2002 | Fraser | |
| 6,589,176 B2 | 7/2003 | Jago et al. | |
| 6,692,438 B2 | 2/2004 | Skyba et al. | |
| 7,657,299 B2 * | 2/2010 | Huizenga | A61B 5/055 382/276 |
| 8,131,336 B2 * | 3/2012 | Liu | A61B 5/02007 382/173 |
| 8,460,194 B2 | 6/2013 | Averkiou et al. | |
| 9,216,008 B2 * | 12/2015 | Hoogi | A61B 8/481 |
| 9,576,357 B2 * | 2/2017 | Averikou | A61B 8/06 |
| 2004/0116807 A1 * | 6/2004 | Amrami | A61B 6/00 600/436 |
| 2004/0265235 A1 * | 12/2004 | Uzgiris | A61K 49/085 424/9.322 |
| 2008/0009702 A1 * | 1/2008 | Liu | A61B 5/02007 600/410 |
| 2008/0200815 A1 * | 8/2008 | Van Der Steen | A61B 8/481 600/467 |
| 2008/0317308 A1 * | 12/2008 | Wu | G06K 9/4638 382/128 |
| 2012/0253190 A1 | 10/2012 | Gauthier et al. | |
| 2013/0204127 A1 * | 8/2013 | Hoogi | A61B 8/481 600/431 |
| 2016/0343134 A1 * | 11/2016 | Averkiou | G06T 7/0016 |

OTHER PUBLICATIONS

Akkus, et al., "New Quantification Methods for Carotid Intra-Plaque Neovascularization Using Contrast-Enhanced Ultrasound", Ultrasound in Medicine and Biology, vol. 40, No. 1, Jan. 1, 2014, pp. 25-36.

Ping-tong Huang, et al., Contrast-Enhanced Sonographic Characteristics of Neovascularization in Carotid Atherosclerotic Plaques, Journal of Clinical Ultrasound, vol. 36, No. 6, Jul./Aug. 2008, pp. 346-351.

Xiong, et al., "Correlation of Carotid Plaque Neovascularization Detected by Using Contrast-enhanced US with Clynical Symptoms", Radiology, vol. 251, No. 2, May 1, 2009, pp. 583-589.

Hoogi, et al., "Carotid Plaque Vulnerability: Quantification of Neovascularization on Contrast-Enhanced Ultrasound With Histopathologic Correlation", American Journal Roentgenology, vol. 196, Feb. 1, 2011, pp. 431-436.

Van den Oord, et al., "Impact of gender on the density of intraplaque neovascularization: A quantitive contrast-enhanced ultrasound study", Atherosclerosis, vol. 233, No. 2, Jan. 24, 2014, pp. 461-466.

Angelelli et al "Interactive Visual Analysis of Contrast-Enhanced Ultrasound Data Based on Small Neighborhood Statistics" Computers & Graphics, vol. 35 (2011) p. 218-226.

* cited by examiner

EVALUATION OF CAROTID PLAQUE USING CONTRAST ENHANCED ULTRASONIC IMAGING

This application is the U.S. National Phase application under 35 U.S.C. § 371 of International Application No. PCT/IB2015/050452, filed on Jan. 21, 2015, which claims the benefit of U.S. Provisional Application Ser. No. 61/930,655, filed Jan. 23, 2014. These applications are hereby incorporated by reference herein.

This invention relates to ultrasonic diagnostic imaging systems and, in particular, to the use of contrast enhanced ultrasonic imaging to evaluate the risk of stroke.

Figures 1, 7:
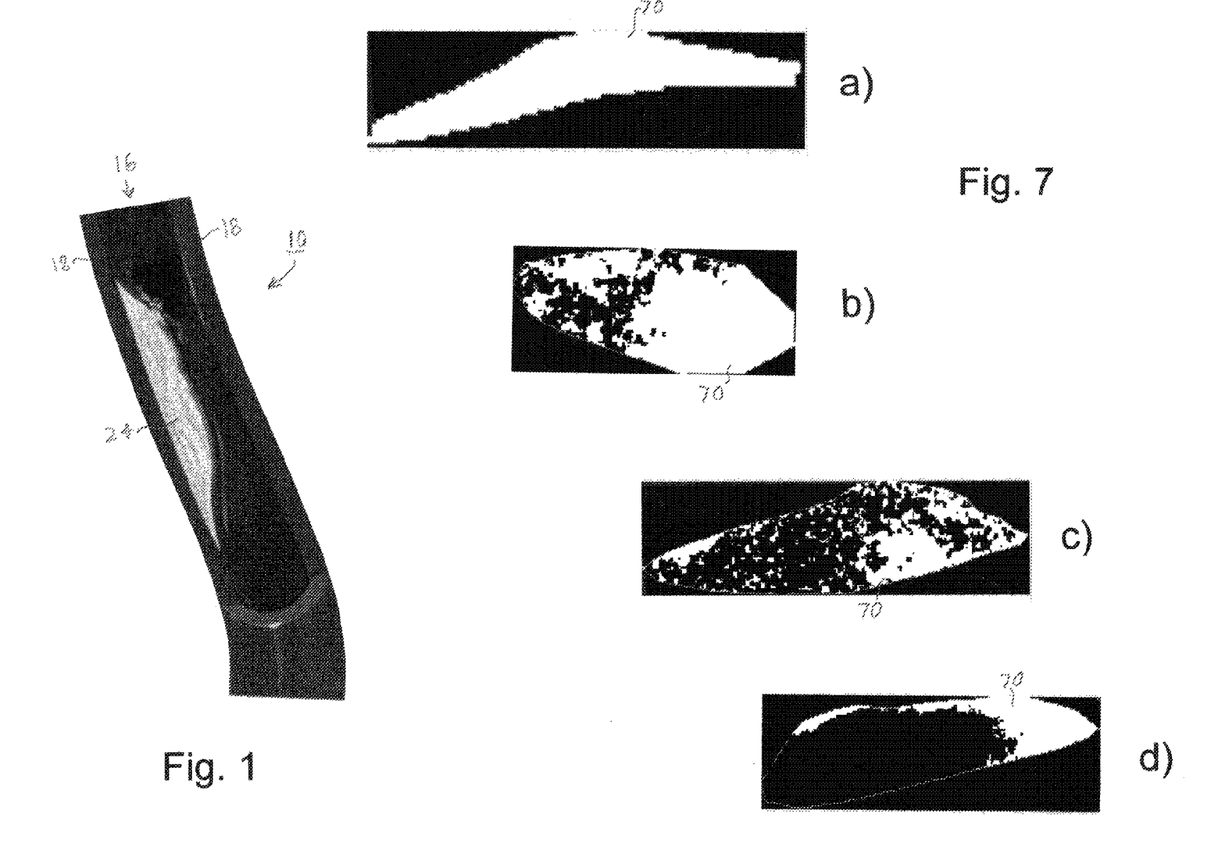
FIG. 1 is an illustration of a blood vessel containing plaque.
FIG. 7 illustrates four qualitative images of atherosclerotic plaque areas with different percentages of perfusion.

The development of plaque in the vascular system, particularly atherosclerosis in the carotid artery, is a common occurrence in many patients. Plaque can build up to a degree where partial and even total occlusion of blood vessels can occur. FIG. 1 illustrates a blood vessel 110 with the vessel wall 18 partially cut away to show the lumen 16 inside, where a plaque build-up 24 is seen. Since the plaque 24 has filled most of the lumen at its thickest point it has partially occluded the flow of blood through the vessel. Not only does the plaque restrict the delivery of fresh blood to tissue and organs downstream of the occlusion, but it can also trap blood clots in the narrowed lumen, blocking all blood flow. An additional, equally serious occurrence can arise from carotid plaque. Since the carotid arteries provide the supply of blood to the brain, particulate matter in the carotid blood flow can pose a risk of cranial vessel occlusion and potentially stroke. Bits of plaque can break loose from the endothelial lining of the carotid arteries and flow to the brain, where they can occlude cranial blood vessels of different dimensions and functionality, depending on the size of the plaque particulates and their path of flow. It would be desirable to be able to identify plaques with this potential so that intervention can be taken to minimize or prevent the potential for stroke.

In accordance with the principles of the present invention, an ultrasonic diagnostic imaging system and method are described which enable the assessment of the risk of stroke from plaque build-up in the carotid artery. Carotid atherosclerotic plaques have areas of plaque neovascularization and perfusion. A study using images from twenty-four patients was conducted to differentiate between symptomatic and asymptomatic patients based on plaque perfusion patterns. In this study the perfusion of carotid plaques was evaluated both qualitatively and quantitatively in order to investigate differences in the perfusion between symptomatic and asymptomatic patients. The patients were injected with 2 ml of Sonovue (Bracco s.p.a., Milan, Italy), an ultrasonic microbubble contrast agent, and one minute ultrasound loops were acquired and saved as the contrast agent flowed through the carotid artery and the microvasculature (neovessels) of the plaque. The ultrasound images can be acquired by B mode imaging which shows the increasing signal intensity from microbubbles which perfuse the plaque. Preferably, the images are acquired by colorflow imaging so that motion of the microbubbles can simultaneously be detected along with signal intensity. Signals exhibiting a high intensity harmonic return together with Doppler-detected motion at the same location are indicative of moving microbubbles at that location. This correlation can be used to distinguish over and reject signal returns from static bright reflectors which are often artifacts. The result is the detection of dynamic contrast agent microflow in the plaque vasculature.

Since the contrast-enhanced ultrasound image sequence is to be used to calculate contrast time-intensity curves (T-I curves) at each point in the plaque, it is important to hold the imaging probe as stationary as possible during image acquisition so that the plaque in the images will spatially correlate over the image sequence. The spatial correlation can be improved by the use of image stabilization, for instance, and/or by detecting and compensating for global motion in the images as might occur due to probe motion or physiological motion from pulsatility or patient movement.

For the assessment of contrast perfusion of the plaque a region-of-interest (ROI) is drawn around the plaque in the images. This delineates the plaque without including any portion of the lumen signal so that the potentially large amplitude signals returning from the contrast agent flowing in the carotid lumen is excluded from the analysis. In one implementation the intensity signal from individual points in the plaque (pixels) can be used, or groups of pixels can be aggregated and the mean intensity of signals from the aggregated groups of pixels used. In another implementation the mean intensity contrast agent signal from within the ROI containing the plaque is sampled across time from image to image to generate time intensity curves of the carotid plaque. These and other techniques can be used to analyze the intensity signal within the plaque. The signal intensity data is assessed by comparing the signal levels against a threshold noise level and by assessing the distribution of values of intensity before and after contrast arrival. If there is a significant difference and distribution of values characteristic of contrast build-up, the pixel is identified as indicating perfusion. The mean T-I curve signal amplitude after the arrival of the microbubbles into the plaque ROI is calculated for each pixel. A qualitative image of the mean intensity signal amplitudes of the pixels can be displayed as colors or intensities of a range of values to indicate qualitatively the vascularization of the plaque.

In accordance with a further aspect of the present invention, quantitative perfusion assessment is performed on the pixel data. The overall number of pixels that have perfusion are divided by the total number of pixels in the delineated image of the plaque. In one implementation a binary grading system is then applied to this result. Zero represents less than 50% of carotid plaque area contained moving microbubbles and 1 represents more than 50% of the carotid plaque area contained moving microbubbles. It was found that for the patients of the study the mean contrast agent intensity signal from the plaques was significantly higher for asymptomatic patients (patients with no history of plaque particulate breakup) than symptomatic patients (patients with a history of plaque particulates in the blood flow). The qualitative analysis results of the study showed that only 25% (3/12) of asymptomatic patients had a score of 0 in comparison to 67% (8/12) of symptomatic patients.

In some embodiments, the present invention provides ultrasound imaging systems, e.g., ultrasonic diagnostic imaging systems for the evaluation of plaque by contrast enhanced ultrasound. The systems can include an ultrasound imaging probe having an array transducer which acquires a sequence of ultrasound images of a plaque during contrast agent delivery. In certain embodiments, the systems can be configured to include processors, memory, and other structures that can serve as a time intensity curve calculator which forms a time intensity curve for each point in a plaque image where contrast is present, and a comparator which identifies pixels in the plaque image where perfusion is present. In some embodiments, the comparator can be operable to compare pixel intensity values before and after contrast arrival in the plaque. The systems can further include a display which displays the degree of perfusion in the plaque. In certain embodiments, the systems can include an image processor which produces an anatomical map of the plaque showing where perfusion is present. In addition, the systems can be configured to include processors, memory, and other structures that can serve as a perfusion quantifier which quantifies the percentage of pixels in the plaque image exhibiting perfusion. The systems, in some embodiments, can include a frame memory which stores the acquired sequence of ultrasound images. In certain embodiments, the systems can be configured to include processors, memory, and other structures that can serve as an image stabilizer, responsive to images stored in the frame memory, which compensates for frame-to-frame motion. In some embodiments, the systems can be configured to include processors, memory, and other structures that can serve as a plaque tracer which outlines a plaque in a carotid image. In some embodiments, the plaque tracer can be controlled via a user control of an ultrasound system control panel such that a user can manually trace the plaque as shown on the display.

In some embodiments, the systems of the present invention can be configured to acquire, using an ultrasound probe, a sequence of ultrasound images of a plaque during contrast agent delivery, calculate a time intensity curve for each point in a plaque image where contrast is present, identify pixels in the plaque image where perfusion is present, and display the degree of perfusion in the plaque. The various hardware components can be included in the system to carry out the various functions. For example, a stand-alone processor configured to receive data, carry out certain functions on the data, and then output the processed data. Alternatively, the system can include several hardware components (e.g., processors) that work together according to encoded software protocols to carry out the various steps. Such software and structures for carrying out the functions would be readily apparent to one of ordinary skill in the art.

Figure 2:
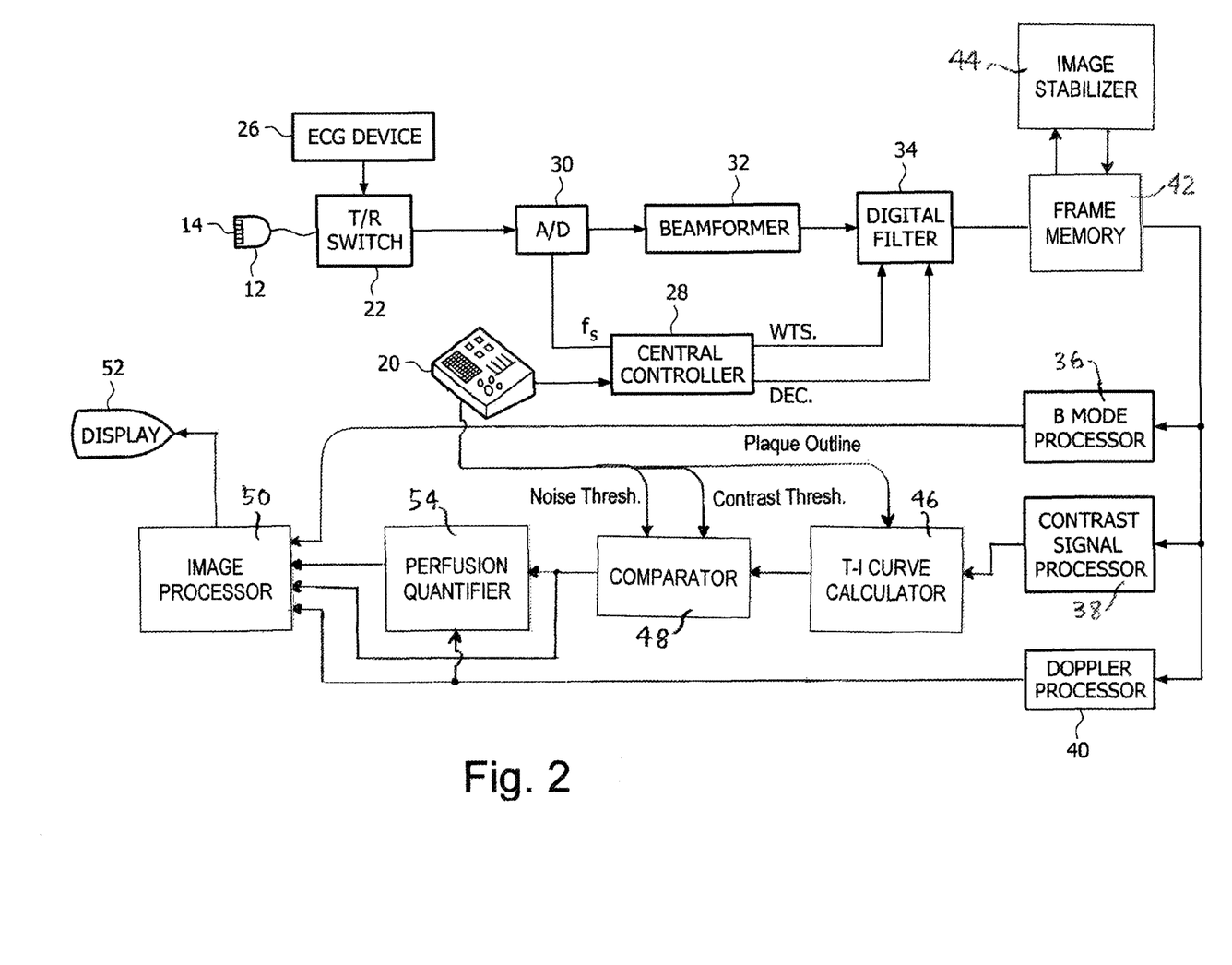
FIG. 2 illustrates in block diagram form an ultrasound system constructed in accordance with the principles of the present invention.

Referring now to FIG. 2, an ultrasound system constructed in accordance with the principles of the present invention is shown in block diagram form. An ultrasonic probe 12 includes an array 14 of ultrasonic transducer elements that transmits and receives ultrasonic signals. The array 14 may be a one dimensional linear or curved array for two dimensional imaging, or may be a two dimensional (2D) matrix of transducer elements for electronic beam steering in three dimensions. The array 14 may also be a one dimensional array that is mechanically swept back and forth by the ultrasonic probe 12 to scan a three dimensional volume of the body. The ultrasonic transducers in the array 14 transmit ultrasonic energy and receive echoes returned in response to this transmission. A transmit/receive ("T/R") switch 22 is coupled to the ultrasonic transducers in the array 14 to selectively couple echo signals from the transducer elements to A/D converters 30 during the receive phase of operation. The times at which the array 14 is activated to transmit signals may be synchronized to an internal system clock, or may be synchronized to a bodily function such as the heart cycle, for which a heart cycle waveform is provided by an electrocardiography (ECG) device 26. When the heartbeat is at the desired phase of its cycle as determined by the waveform provided by the ECG device 26, the ultrasonic probe 12 is commanded to acquire an ultrasonic image. In the conduct of the method of the present invention, a continuous sequence of real time image frames of a carotid artery is acquired as blood containing contrast agent begins to perfuse the vasculature of plaques in the carotid.

Echoes from the transmitted ultrasonic energy are received by the transducer elements of the array 14, which generate echo signals that are coupled through the T/R switch 22 and digitized by analog to digital ("A/D") converters 30 when the system uses a digital beamformer. Analog beamformers may alternatively be used. The A/D converters 30 sample the received echo signals at a sampling frequency controlled by a signal $f_s$ generated by a central controller 28. The desired sampling rate dictated by sampling theory is at least twice the highest frequency of the received passband, and might be on the order of 30-40 MHz. Sampling rates higher than the minimum requirement are also desirable. Control of the ultrasound system and the setting of various parameters for imaging, such as probe selection, are affected by user manipulation of the controls of the user interface of a control panel 20 which is coupled to and applies its control through the central controller 28.

The echo signal samples from the individual transducer elements of the array 14 are delayed and summed by a beamformer 32 to form digital coherent echo signals. For 3D imaging with a two dimensional array, it is preferable to partition the beamformer 32 between a microbeamformer located in the ultrasonic probe 12 and the main beamformer in the system mainframe as described in U.S. Pat. No. 6,013,032 (Savord) and U.S. Pat. No. 6,375,617 (Fraser). The digital coherent echo signals are then filtered by a digital filter 34. In this embodiment, the probe transmit frequency and the receiver frequency are individually controlled so that the beamformer 32 is free to receive a band of frequencies which is different from that of the transmitted band such as a harmonic frequency band for detection of harmonic contrast agents. The digital filter 34 bandpass filters the signals, and can also shift the frequency band to a lower or baseband frequency range. The digital filter 34 could be a filter of the type disclosed in U.S. Pat. No. 5,833,613 (Averkiou et al.), for example. Filtered echo signals from scans of successive image frames are stored in a frame memory 42. Since it is important for the calculation of precise time intensity curves that pixels of successive image frames be spatially aligned, registration of the successive frames is performed by an image stabilizer 44. This spatial correlation is preferably performed by use of an image stabilizer as described in U.S. Pat. No. 6,589,176 (Jago et al.)

The spatially aligned image frames are coupled from the frame memory 42 to a B mode processor 36 for conventional B mode processing and the production of 2D B mode images. The image frames, and particularly their harmonic contrast agent signal content returned from microbubbles, are coupled to a contrast signal processor 38. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950 (Averkiou et al.)

The filtered echo signals from the frame memory 42 are also coupled to a Doppler processor 40 for conventional Doppler processing to produce velocity and/or power Doppler images. The output signals from these three processors 36, 38, 40 may be scan converted and displayed as planar 2D images, for which their outputs are coupled to an image processor 50 for a display 52. Their output images, when 3D scanning is performed, may also be rendered as three dimensional (3D) images, which may also be processed for display on display 52.

Figure 4A:
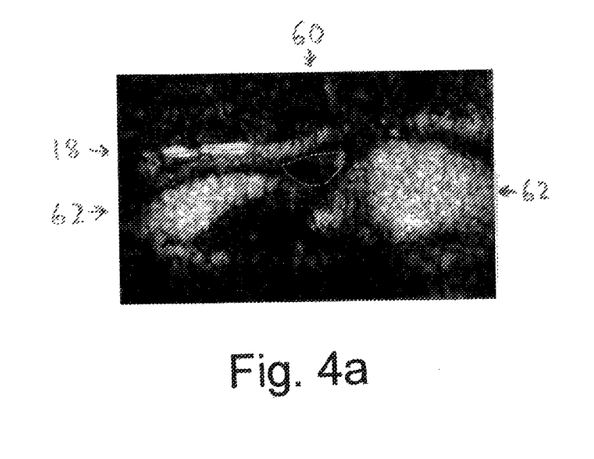
FIGS. 4a and 5a are ultrasound images in which plaques in carotid arteries have been outlined.
Figure 5A:
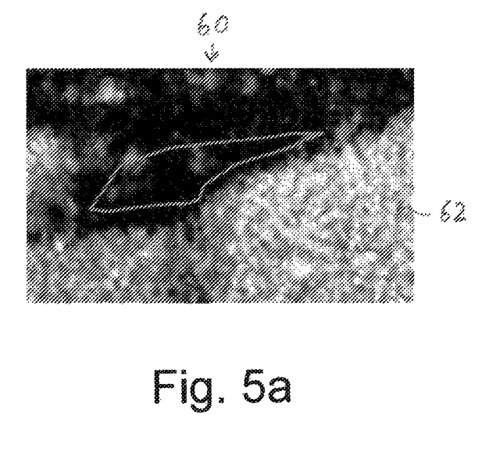

After a sequence of image frames has been acquired during contrast agent delivery and stored in the frame memory 42, the user may review the images in the B mode, examples of which are shown in FIGS. 4a and 5a. These are images of carotid arteries containing plaque. The large bright areas 62 in the images are regions of blood flow containing contrast agent, which return particularly strong (and hence brightly displayed) echo signals. The vessel wall 18 is distinctly shown in FIG. 4a with its vasculature perfused with contrast. A discerning user can also spot plaques in the images. Unlike the lumen of the vessel, the microvasculature of plaques will contain much less contrast and hence appear as darker areas in the images. The plaque can be traced a variety of ways. For example, the system can include a plaque tracer that can automatically or under manual control be used to trace the plaque as displayed on a screen. For example, the user can trace or outline these plaques when they are spotted, and these outlined plaque areas are processed as described below. The plaque tracer can be included in the system as a stand-alone processor configured to receive data, carry out certain functions on the data, and then output the processed data. Alternatively, the system can include several hardware components (e.g., processors) that work together according to encoded software protocols to carry out the various steps performed by the T-I curve calculator. Such software and structures for carrying out the functions would be readily apparent to one of ordinary skill in the art. FIGS. 4a and 5a each contain a plaque 60 which the user has outlined using a control on the control panel 20 such as a trackball or mouse.

Figure 3:
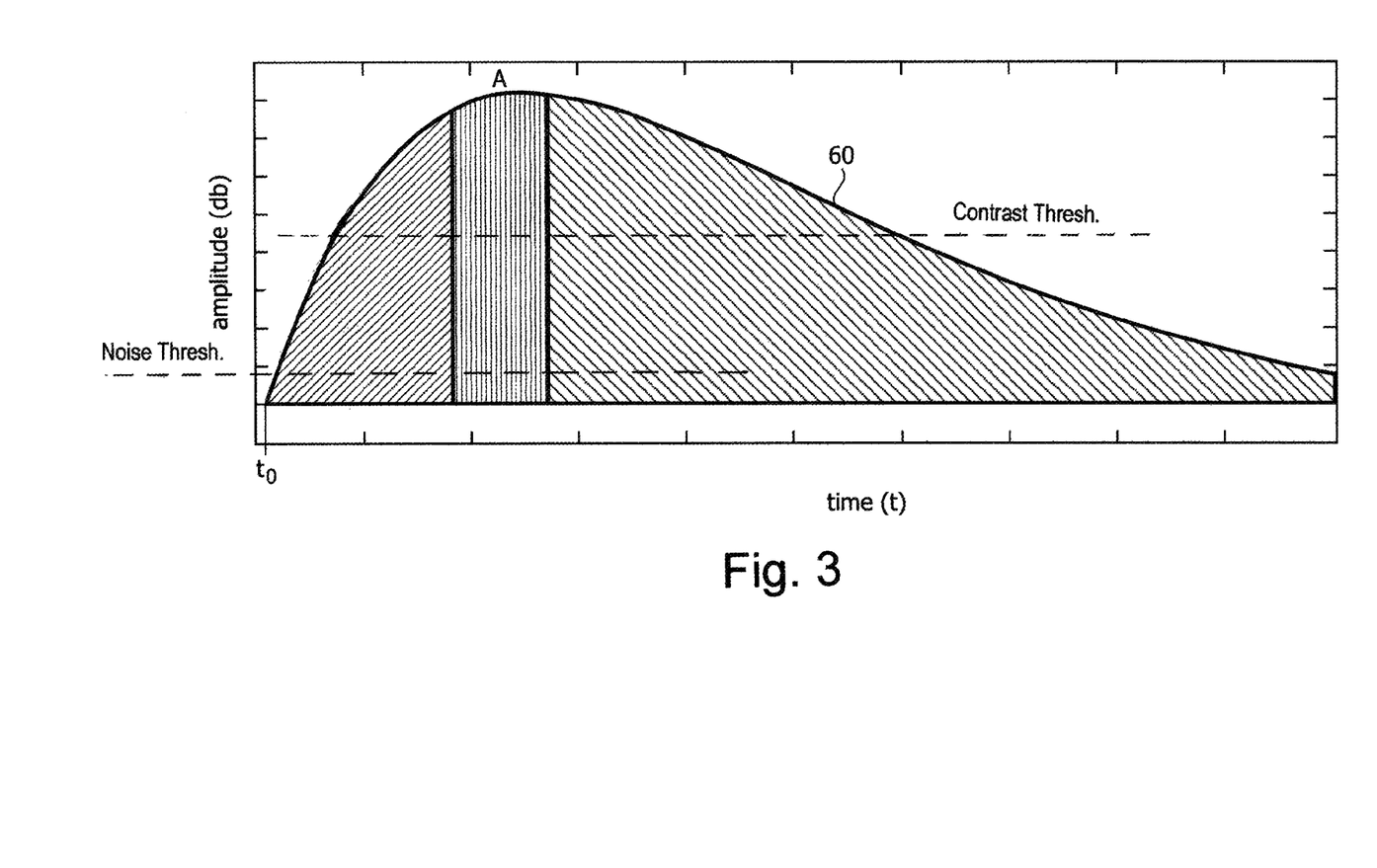
FIG. 3 illustrates a contrast time-intensity curve.
Figure 4B:
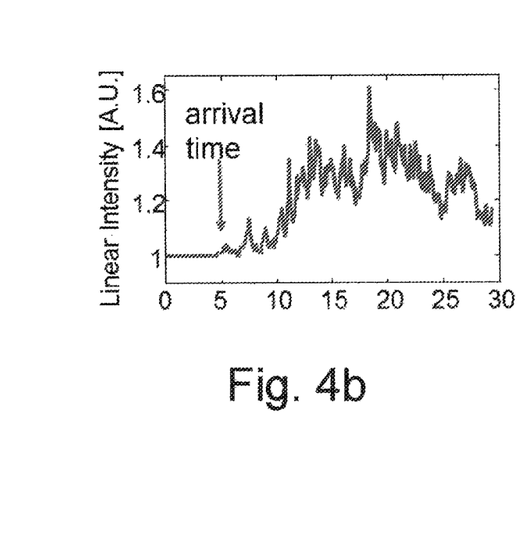
FIGS. 4b and 5b illustrate the change in signal intensity in the plaque areas of FIGS. 4a and 5a with the arrival of contrast agent flows in the plaques.
Figure 5B:
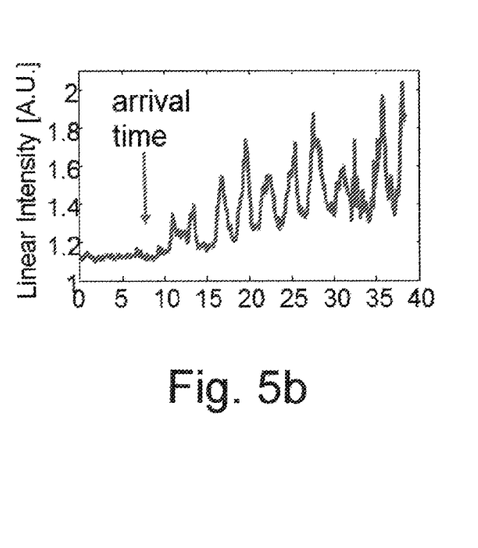

The identification of the plaque outline area 60 is coupled to a time-intensity (T-I) curve calculator 46 as shown in FIG. 2. The time intensity curve calculator as shown can be included in the system as a stand-alone processor configured to receive data, carry out certain functions on the data, and then output the processed data. Alternatively, the system can include several hardware components (e.g., processors) that work together according to encoded software protocols to carry out the various steps performed by the T-I curve calculator. Such software and structures for carrying out the functions would be readily apparent to one of ordinary skill in the art. The T-I curve calculator then processes the pixels of the plaques in the sequence of image frames to form a time intensity curve for each point in the plaque. When contrast agent is flowing at a particular point in the plaque during contrast delivery, the contrast agent will build up following its initial arrival time as shown in FIGS. 4b and 5b, which correspond to points in FIGS. 4a and 5a, respectively. The T-I curve calculator processes this build-up in contrast signal intensity to produce a time intensity curve as described in US pat. pub. no. US2012/0253190 (Gauthier et al.) and U.S. Pat. No. 8,460,194 (Averkiou et al.) An idealized time intensity curve 60 is shown in FIG. 3. It is seen that this curve begins to increase following the initial arrival of contrast agent at time t0, builds up to a maximum amplitude A at the time of maximum contrast perfusion, then gradually declines as the contrast agent flows out of that region of the body.

A comparator 48 performs several checks on the time intensity curve data to verify that contrast agent is indeed present at each point for which a time intensity curve has been produced. The comparator as shown can be included in the system as a stand-alone processor configured to receive the curve data and verify the presence of contrast agent. Alternatively, the system can include several hardware components (e.g., processors) that work together according to encoded software protocols to carry out the various steps performed by the comparator. Such software and structures for carrying out the functions would be readily apparent to one of ordinary skill in the art. (If there is no flow of contrast at a point, there will be no time intensity curve for that point.). One check is to compare the distribution of the intensity values before the arrival of the contrast agent (i.e., noise distribution) with the distribution of values after the arrival of the contrast agent. In one implementation the Kolmogorov-Smirnov two-sample test is used. Additional statistical tests or methods can also be used to compare the intensity distribution. If the distribution of intensity values before the arrival of the contrast agent, i.e., noise, is statistically different from the distribution of values after the arrival of the contrast agent, then that pixel or group of pixels is considered to be perfused. In another implementation the amplitude of the time intensity curve is compared against a noise threshold. Amplitude spikes from artifacts in the image data are thereby eliminated from consideration as contrast. Another test is to compare the maximal amplitude region of the curve 60 against a contrast threshold. This threshold is a level which a contrast agent response should exceed for a sustained period of time. When the time intensity curve from a point in the plaque region passes both of these tests, it is confirmed that a flow of contrast agent was present at the point.

A qualitative image of perfusion may now be formed for the plaque region. The maximum intensity amplitudes A or the mean signal intensity of the time intensity curves or the statistical probability of perfusion at the points where contrast was present may be mapped to corresponding colors of a color map, and the color map may be displayed as a parametric overlay over a B mode image of the plaque region as described in U.S. Pat. No. 6,692,438 (Skyba et al.) For instance, region of contrast perfusion may be displayed in varying shades of red and areas with no perfusion may be displayed as black. The user can thus observe the degree of perfusion of the plaque, the degree to which it contains vascularization. FIG. 7 illustrates four regions of plaque 70 with varying degrees of perfusion, each shown against a black background. Within each plaque region, points which are perfused are shown in white and points with no perfusion are shown in black. In FIG. 7a the plaque area 70 is 100% perfused. In FIG. 7b the plaque area 70 is 76% perfused. In FIG. 7c the plaque area 70 is 38% perfused and in FIG. 7d the plaque area 70 is only 26% perfused.

In accordance with a further aspect of the present invention, the overall perfusion of a plaque is quantified by a perfusion quantifier 54. The perfusion comparator as shown can be included in the system as a stand-alone processor configured to receive data and quantify perfusion of the plaque. Alternatively, the system can include several hardware components (e.g., processors) that work together according to encoded software protocols to carry out the various steps performed by the perfusion quantifier. Such software and structures for carrying out the functions would be readily apparent to one of ordinary skill in the art. The overall number of pixels in a plaque area 70 that have perfusion are divided by the total number of pixels in the image of the plaque. In one implementation a binary grading system is then applied to this result. Zero represents less than 50% of a carotid plaque area 70 contained moving microbubbles and 1 represents more than 50% of the carotid plaque area contained moving microbubbles. The threshold at which zero and 1 are determined can change with the perfusion detection technique, the sensitivity of the technique, the statistical probability deemed significant and any subsequent experimental or clinical studies conducted to determine the optimal clinical threshold. To enhance the reliability of these results, the perfusion quantifier receives the Doppler flow map of the plaque. Each point where a valid time intensity curve of contrast was found should also be found to exhibit motion at the corresponding point in the Doppler flow map, since the contrast agent must be flowing at the point. The presence of Doppler-identified motion at a point where contrast and a time intensity curve were found confirms the point as having contrast present. A highly reliable quantification of perfusion is thereby produced and displayed on the display 52. It has been found that the mean contrast agent intensity signal from a plaque is significantly higher for asymptomatic patients (patients with no history of plaque particulate breakup) than symptomatic patients, patients with a history of plaque particulates in the blood flow. The categorization of the risk of stroke can be further complicated in cases where there is inter-plaque hemorrhage, presence of thrombus or any disruption of the microvasculature of the plaque. The clinical predictors of stroke are to be assessed and investigated based on the perfusion detection techniques outlined herein.

In some embodiments, the present invention includes methods for evaluating plaque. For example, the present invention includes methods of evaluating plaque with contrast enhanced ultrasound. The methods can include acquiring a sequence of ultrasound images during contrast agent delivery of a carotid artery having plaque, identifying a plaque in an ultrasound image, comparing intensity values at locations in the plaque before and after the arrival of contrast, identifying points in the image having perfusion, and displaying the degree of perfusion in the plaque. In some embodiments, the identifying a plaque can include outlining a plaque in one of the ultrasound images. In certain embodiments, the methods can include forming a time intensity curve at each point in the plaque where contrast is present. The methods can include forming an anatomical map of the plaque which shows points where perfusion has been identified and/or quantifying the percentage of points in an image of the plaque which exhibit perfusion. In certain embodiments, the methods can include compensating for frame-to-frame motion in the sequence of ultrasound images and/or correlating points in the image of the plaque where perfusion has been identified with points in the image of the plaque where motion is present. The methods can also include forming a time intensity curve of the mean signal from within the plaque to identify the arrival of the contrast agent in the plaque.

Figure 6:
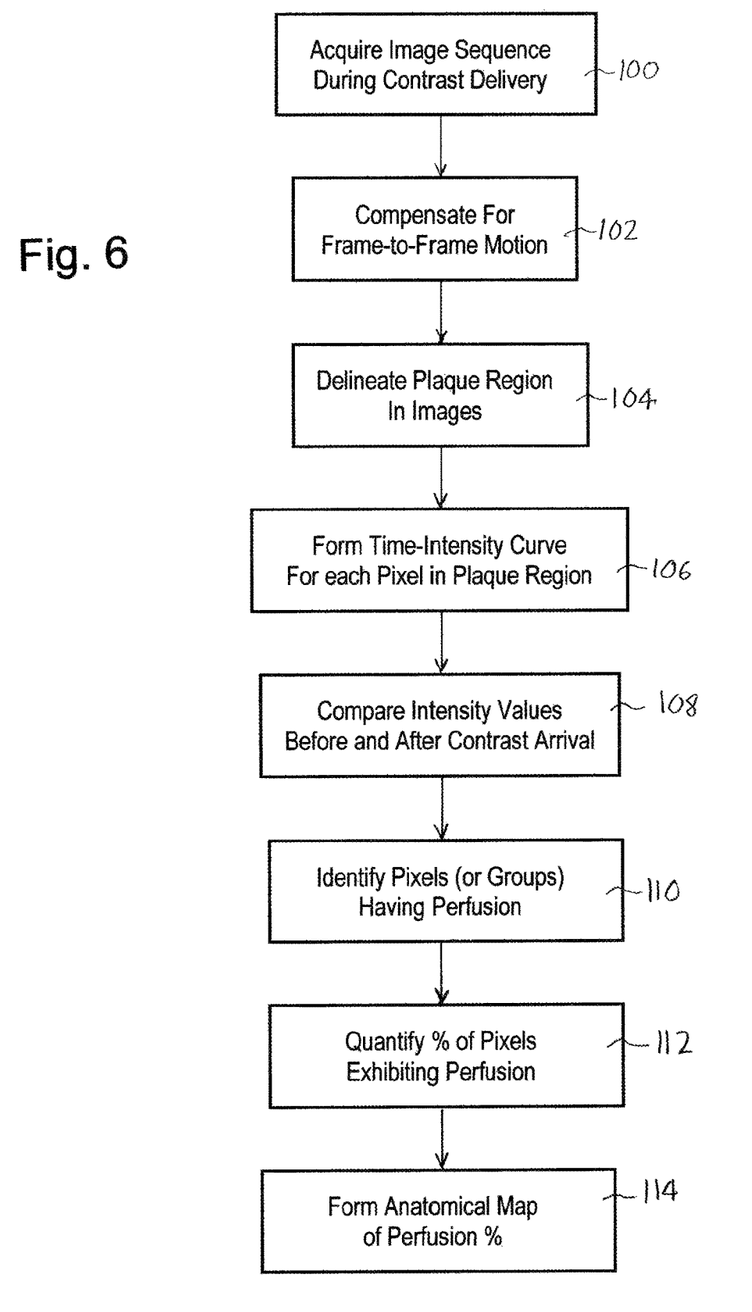
FIG. 6 is a flowchart illustrating the steps of a method of the present invention.

FIG. 6 is a flowchart of a method of the present invention. In step 100 an image sequence of a carotid artery is acquired, typically lasting at least a minute following infusion of contrast. This captures images of any plaque microflow containing the contrast agent. In step 102 frame-to-frame motion is compensated using motion compensation techniques so that the plaque is in registration with the same pixels over the image sequence. In step 104 the plaque region is delineated in the images as by tracing. In step 106 a time-intensity curve is formed for each pixel in the plaque region. The contrast arrival time may be estimated based on a given increase of the mean intensity within the whole plaque, groups of pixels or individual pixels above the noise level. In step 108 the intensity values at each point where contrast is present is compared before and after contrast arrival and, if there is a significant difference, the pixel is identified as having perfusion. This identification of perfusion is done for every pixel or group of pixels (step 110). In step 112 the percentage of the total pixels in the plaque exhibiting perfusion is quantified. This is done by dividing the overall number of pixels that have perfusion by the total number of pixels in the image of the plaque. In step 114 a qualitative result is presented by forming an anatomical map of the percentage of the plaque that is perfused as shown in FIG. 7.

What is claimed is:

1. An ultrasonic diagnostic imaging system for the evaluation of plaque by contrast enhanced ultrasound, the system comprising:
   an ultrasound imaging probe having an array transducer configured to acquire a sequence of ultrasound images of a plaque region in a carotid artery during contrast agent delivery;
   a time intensity curve calculator configured to form a plurality of time intensity curves for the plaque region, wherein the plaque region comprises a plurality of pixels and wherein the plurality of time intensity curves includes a time intensity curve for each pixel in the plurality of pixels of the plaque region;
   a comparator configured to determine, for each pixel in the plurality of pixels in the plaque region, whether contrast is present in a given pixel based on the time intensity curve for the given pixel; and
   a display configured to display the degree of perfusion in the plaque region.

2. The ultrasonic diagnostic imaging system of claim 1, further comprising an image processor configured to produce an anatomical map of the plaque region showing where perfusion is present.

3. The ultrasonic diagnostic imaging system of claim 1, further comprising a perfusion quantifier configured to quantify the percentage of pixels in the plaque region exhibiting perfusion.

4. The ultrasonic diagnostic imaging system of claim 1, further comprising a frame memory configured to store the acquired sequence of ultrasound images.

5. The ultrasonic diagnostic imaging system of claim 4, further comprising an image stabilizer, configured to compensate for frame-to-frame motion.

6. The ultrasonic diagnostic imaging system of claim 1, further comprising a plaque tracer which outlines a plaque in a carotid image.

7. The ultrasonic diagnostic imaging system of claim 6, wherein the plaque tracer further comprises a user control of an ultrasound system control panel.

8. The ultrasonic diagnostic imaging system of claim 1, wherein the comparator is further operable to compare pixel intensity values before and after contrast arrival in the plaque region.

9. A method of evaluating plaque with contrast enhanced ultrasound, the method comprising:

acquiring a sequence of ultrasound images during contrast agent delivery of a carotid artery having plaque;

identifying a plaque region in an ultrasound image of the sequence, wherein the plaque region includes a plurality of pixels;

forming a time intensity curve for each pixel of the plurality of pixels in the plaque region;

for each of the plurality of pixels and associated time intensity curve, comparing intensity values of the pixel before and after the arrival of contrast to determine whether contrast is present;

identifying, based on the comparison, one or more pixels in the image having perfusion; and displaying the degree of perfusion in the plaque region.

10. The method of claim 9, wherein identifying a plaque region further comprises outlining a plaque region in one of the ultrasound images.

11. The method of claim 9, further comprising forming an anatomical map of the plaque region which shows pixels where perfusion has been identified.

12. The method of claim 9, further comprising quantifying the percentage of pixels in an image of the plaque region which exhibit perfusion.

13. The method of claim 9, further comprising compensating for frame-to-frame motion in the sequence of ultrasound images.

14. The method of claim 9, further comprising correlating pixels in the image of the plaque region where perfusion has been identified with pixels in the image of the plaque region where motion is present.

15. The method of claim 9, further comprising forming a time intensity curve of the mean signal from within the plaque region to identify the arrival of the contrast agent in the plaque region.

* * * * *